United States Patent
Nord et al.

(10) Patent No.: US 8,160,203 B2
(45) Date of Patent: Apr. 17, 2012

(54) CALCULATION OF PROBABLE ACCUMULATED DOSAGES BASED ON PATIENT MOVEMENT

(75) Inventors: Janne Ilmari Nord, Espoo (FI); Sami Pekka Siljamäki, Espoo (FI)

(73) Assignee: Varian Medical Systems International AG, Postfach (CH)

( * ) Notice: Subject to any disclaimer, the term of this patent is extended or adjusted under 35 U.S.C. 154(b) by 1210 days.

(21) Appl. No.: 11/903,822

(22) Filed: Sep. 24, 2007

(65) Prior Publication Data

US 2009/0082608 A1    Mar. 26, 2009

(51) Int. Cl.
*A61N 5/10* (2006.01)
(52) U.S. Cl. ............................. 378/65; 378/95
(58) Field of Classification Search ................. 378/65, 378/95
See application file for complete search history.

(56) References Cited

U.S. PATENT DOCUMENTS

| | | | | |
|---|---|---|---|---|
| 7,206,377 B2* | 4/2007 | Svatos | ............................ | 378/65 |
| 7,856,082 B2* | 12/2010 | Flynn et al. | ..................... | 378/65 |
| 2004/0146141 A1* | 7/2004 | Svatos | ............................ | 378/65 |
| 2009/0110145 A1* | 4/2009 | Lu et al. | .......................... | 378/65 |
| 2009/0234626 A1* | 9/2009 | Yu et al. | ........................... | 703/11 |
| 2010/0189220 A1* | 7/2010 | Flynn et al. | ..................... | 378/65 |

\* cited by examiner

*Primary Examiner* — Edward Glick
*Assistant Examiner* — Thomas R Artman
(74) *Attorney, Agent, or Firm* — Vista IP Law Group, LLP

(57) ABSTRACT

A stochastic patient movement model and a dosage delivery plan are used to determine probabilities of dosages received by a target volume during a radiation treatment. The stochastic patient movement model is created by identifying possible sequences of patient positions during the treatment with probabilities specified for each. The dosage delivery plan specifies dosage levels and radiation locations over time. Accumulated dosages are calculated for each sequence of patient positions and the dosage delivery plan. The specified probability for each sequence is then correlated to the accumulated dosage for that sequence.

20 Claims, 5 Drawing Sheets

CALCULATION OF PROBABLE ACCUMULATED DOSAGES BASED ON PATIENT MOVEMENT

BACKGROUND

1. Field of Invention

This invention is in the field of radiation therapy and more specifically related to use of patient positions to calculate an accumulated dosage.

2. Description of Related Art

To treat cancer, a patient may undergo a radiation treatment known as intensity-modulated radiation therapy (IMRT). During this radiation treatment, a beam of high energy particles and/or x-rays is directed towards a cancerous tumor in the patient in order to kill the tumor. Based on the shape, size, and/or position of the tumor, the beam rotates around the patient and delivers the radiation from different directions according to a dosage delivery model. The dosage delivery model is developed so as to deliver an effective dosage of radiation while minimizing the amount of radiation delivered to healthy locations in the body. The dosage delivery model typically includes a shape of the beam and an amount of radiation to deliver at each beam position.

As is known is the art, a traditional dosage volume histogram (DVH) is oftentimes generated to evaluate the effectiveness of radiation delivered to a patient according to the dosage delivery model. The DVH depicts the amount of radiation received by a specific volume, for example, the heart, lungs, spine, tumor, or the like. To select a dosage delivery model, a doctor can compare DVHs for multiple volumes and/or DVHs based on more than one dosage delivery model.

Figure 1:
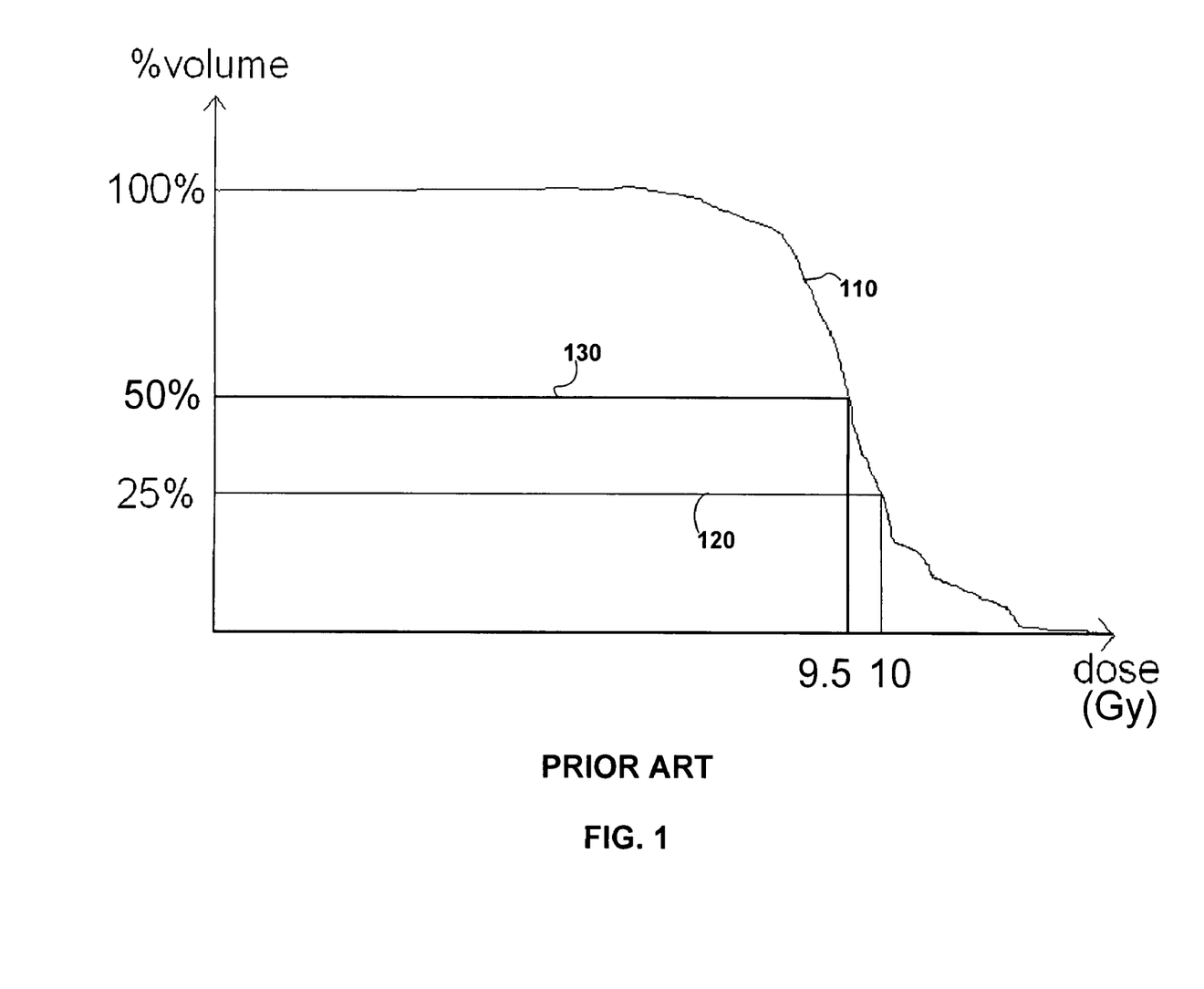
FIG. 1 is a dosage volume histogram as is known in the prior art.

FIG. 1 depicts an exemplary DVH as is known in the prior art. A curve 110 on the DVH represents the dosage received by a target volume, such as an organ. The curve 110 is interpreted by a doctor as indicating that a dose of at least ten Grays is received by 25% of the total volume of the organ in question. This single data point is typically represented by a histogram 120. Likewise, another data point is represented by a histogram 130. Histogram 130 indicates that a dose of at least 9.5 Grays is received by 50% of the total volume of the organ in question. However, the DVH is based on idealized positioning of the patient and does not account for movement of the patient, thus the relative dosages illustrated by the DVH may have little correspondence to what actually occurs within the patient during radiation treatment.

SUMMARY

Systems and methods for determining probabilities of dosages received by a target volume during a radiation treatment are provided. To determine the probabilities of dosages, sequences of patient positions having a specified probability of actually occurring and a dosage delivery model are used. Accumulated dosages are calculated for each sequence of patient positions and the dosage delivery plan. Because the movement of the patient affects the accumulated dosage, the probability of an identified sequence of patient positions used to calculate the accumulated dosage is correlated to the accumulated dosage. The calculation of the accumulated dosage and the correlation to the probability of a sequence of patient positions is repeated using other identified sequences of patient positions. The accumulated dosage is separately calculated for more than one target volume such as a cancerous tumor, a lung, or a spinal cord and/or additional dosage delivery models. Using several accumulated dosages and correlated probabilities, a probability dosage volume histogram that indicates the accumulated dosages in a target volume and includes the correlated probabilities may be generated.

According to some embodiments, a method comprises identifying a first sequence of patient positions each corresponding to a time slot and identifying a second sequence of patient positions each corresponding to a time slot based on an ideal movement model, an initial phase probability model, and a dynamic transition model. A first probability is specified for the first sequence of patient positions and a second probability is specified for the second sequence of patient positions. A first dosage delivery model specifying a dosage level and a location corresponding to each time slot is received. A first accumulated dosage for the first sequence of patient positions based on the first dosage delivery model and a second accumulated dosage for the second sequence of patient positions based on the first dosage delivery model is calculated. The first probability of the first sequence of patient positions is correlated to the first accumulated dosage and the second probability of the second sequence of patient positions is correlated to the second accumulated dosage.

According to some embodiments, a system comprises a stochastic patient movement model module, an accumulated dosage calculator, and a probability module. The stochastic patient movement model module configured to identify a first sequence of patient positions each corresponding to a time slot and a second sequence of patient positions each corresponding to a time slot based on an ideal movement model, an initial phase probability model, and a dynamic transition model, and specify a first probability for the first sequence of patient positions and a second probability for the second sequence of patient positions. The accumulated dosage calculator configured to calculate a first accumulated dosage for the first sequence of patient positions based on a dosage delivery model specifying a dosage level and a location corresponding to each time slot and a second accumulated dosage for the second sequence of patient positions based on the dosage delivery model. The probability module configured to correlate the first probability of the first sequence of patient positions to the first accumulated dosage and correlate the second probability of the second sequence of patient positions to the second accumulated dosage.

According to some embodiments, a computer-readable medium has embodied thereon instructions executable by a processor for performing a method for calculating accumulated dosages based on patient movement. The method comprises identifying a first sequence of patient positions each corresponding to a time slot and identifying a second sequence of patient positions each corresponding to a time slot based on an ideal movement model, an initial phase probability model, and a dynamic transition model. A first probability is specified for the first sequence of patient positions and a second probability is specified for the second sequence of patient positions. A dosage delivery model specifying a dosage level and a location corresponding to each time slot is received. A first accumulated dosage for the first sequence of patient positions based on the dosage delivery model and a second accumulated dosage for the second sequence of patient positions based on the dosage delivery model is calculated. The first probability of the first sequence of patient positions is correlated to the first accumulated dosage and the second probability of the second sequence of patient positions is correlated to the second accumulated dosage.

DETAILED DESCRIPTION

Systems and methods for determining the probability of an accumulated dosage of a radiation delivery plan based on sequences of patient positions during a radiation treatment are provided. In a stochastic patient movement model, the sequences of patient positions are identified based on an ideal movement model, an initial phase probability model, and a dynamic transition model. Each of the sequences of patient positions has a specified probability of being an actual sequence of patient positions during the radiation treatment. The patient positions within the sequences each correspond to a time slot. A dosage delivery model specifies a dosage level and a location at each time slot. To calculate an accumulated dosage, an expected dosage for a target volume at each time slot is calculated based on the dosage delivery model specified location and the patient position within the first sequence of patient positions. The accumulated dosage is the sum of the expected dosages. The probability of the first sequence of patient positions is correlated to the accumulated dosage.

In an embodiment, the accumulated dosage is calculated for additional sequences of patient positions to generate a probability dosage volume histogram for the target volume and the dosage delivery model. The probability dosage volume histogram can be used by a physician to evaluate how sensitive the dosage delivery model is to patient movement during the radiation treatment. The systems and methods described herein may be used to calculate additional probability dosage volume histograms for various target volumes based on a single dosage delivery model. Further, the accumulated dosages and the probabilities correlated to each for multiple dosage delivery models may be calculated.

Figure 2:
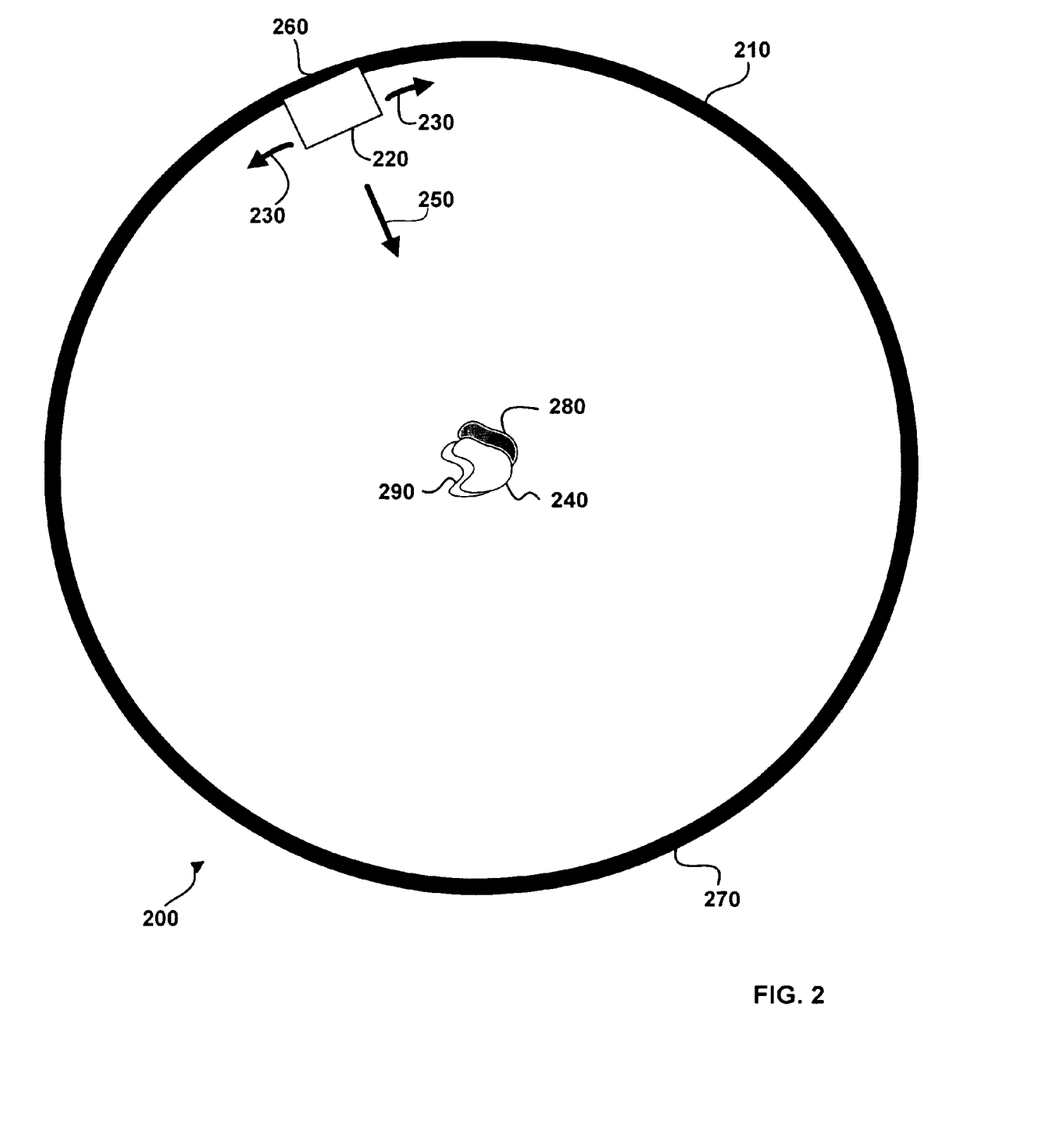
FIG. 2 illustrates a radiation treatment system including a 360 degree gantry, according to various embodiments of the invention.

FIG. 2 illustrates a Radiation Treatment System generally designated 200 and including a 360 degree Gantry 210 configured to support and move an Aperture 220. The Gantry 210 is configured to move the Aperture 220 and optionally part of a beam source (not shown) in directions 230. As the Aperture 220 is moved around a Target Volume 240, the beam of radiation travels from the Aperture 220 to the Target Volume 240 from a variety of directions. For example, at the position of the Aperture 220 illustrated in FIG. 2, a radiation beam is directed in a Direction 250.

As the Aperture 220 is moved around the Target Volume 240, the projection of the Target Volume 240 onto the Aperture 220 changes according to the three-dimensional shape of the Target Volume 240. This changing projection is one of the factors that is used to determine an accumulated dosage. The projection of the Target Volume 240 will be approximately the same when the Aperture 220 is positioned in opposing positions around the Gantry 210. For example, the projections from a Position 260 and a Position 270, being 180 degrees apart along the Gantry 210, will be approximately the same.

The Target Volume 240 may comprise, for example, a cancerous tumor that neighbors healthy tissue. Due to patient movements, such as breathing, the Target Volume 240 may change position during a radiation treatment. For example, the Target Volume 240 may move to Positions 280 and/or 290 during a normal breathing cycle. This movement is typically not accounted for in prior art methods of calculating a DVH. Because of these patient movements, the radiation beam may not always reach the Target Volume 240 or the expected portion of the Target Volume 240. Further, the healthy tissue neighboring the Target Volume 240 may receive an unwanted dosage of radiation. The stochastic patient movement model is used to statistically calculate an expected dosage based on the probability of a sequence of patient positions during the radiation treatment.

Figure 3:
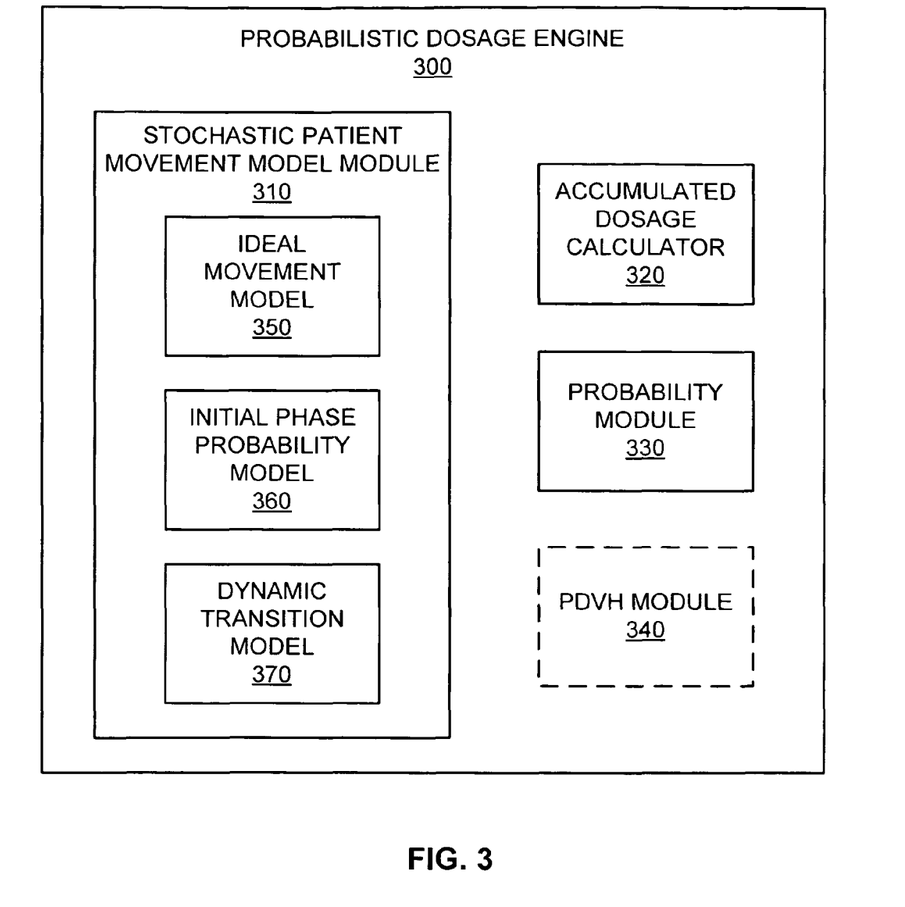
FIG. 3 is a block diagram of a probabilistic dosage engine, according to various embodiments of the invention.

FIG. 3 is a block diagram of a probabilistic dosage engine 300, according to various embodiments of the invention. The probabilistic dosage engine 300 comprises a stochastic patient movement model module 310, an accumulated dosage calculator 320, a probability module 330, and an optional probability dosage volume histogram (PDVH) module 340. The stochastic patient movement model module 310 further comprises an ideal movement model 350, an initial phase probability module 360, and a dynamic transition model 370.

The probabilistic dosage engine 300 comprises one or more computing devices including computer readable media, a processor, and/or logic. For example, the probabilistic dosage engine 300 may comprise a processor (not shown) configured to execute computing instructions stored in the computer readable medium (not shown). These instructions may be embodied in software and divided into the stochastic patient movement model module 310, the accumulated dosage calculator 320, the probability module 330, and the optional probability dosage volume histogram (PDVH) module 340. The computer readable medium can be an IC memory chip, such as, for example, static random access memory (SRAM), dynamic random access memory (DRAM), synchronous DRAM (SDRAM), non-volatile random access memory (NVRAM), and read only memory (ROM), such as erasable programmable ROM (EPROM), electrically erasable programmable ROM (EEPROM), and flash memory. Alternatively, the probabilistic dosage engine 300 may comprise one or more chips with logic circuitry, such as, for example, an application specific integrated circuit (ASIC), a processor, a microprocessor, a microcontroller, a field programmable gate array (FPGA), a programmable logic device (PLD), a complex programmable logic device (CPLD), or other logic device.

The stochastic patient movement model module 310 is configured to identify sequences of patient positions based on the ideal movement model 350, the initial phase probability model 360, and the dynamic transition model 370. The patient positions in the sequences each correspond to a time slot. The stochastic patient movement model module 310 additionally specifies an overall probability of the sequence actually occurring during a radiation treatment. According to some embodiments, the sequences of patient positions are stored in a data structure such as a matrix or a tree. The stochastic patient movement model module 310 comprises discrete or nearly continuous data. The stochastic patient movement model module 310 may represent a respiratory, cardiac, or other patient movement.

The ideal movement model 350 is based on a series of images each image being associated with a different position of the patient as is known in the art. The images may be x-ray images, computed tomography (CT) images, or the like. From these images, a series of deformation fields are calculated to describe the movement of points within the patient. Methods of using these deformation fields to approximate positions of a patient's organ(s), or other target volumes, over a period of time are known in the art. Alternatively, the ideal movement model 350 comprises continuous, or nearly continuous, movement data. The ideal movement model 350 is based on data collected from a plurality of patients and/or from the patient undergoing radiation treatment.

The initial phase probability model 360 comprises at least a portion of the positions in the ideal movement model 350 and a probability of each being a starting position when the radiation treatment begins, as is known in the art. In some embodiments, the probabilities of each patient position are equal to one another. In other embodiments, the initial phase probability model 360 has some positions with a higher probability and others with a lower or zero probability.

The initial phase probability model 360 may be based on patient-specific or treatment-specific data. For example, if the radiation is delivered to the patient during a portion of the breathing cycle, such as the beginning of an inhale cycle, the patient position corresponding to the start of an inhale has a higher probability than the patient positions corresponding to an exhale.

The dynamic transition model 370 comprises probabilities of a next position in a sequence of patient positions and defines the time slots in the sequences of patient movement sequences as is known in the art. In various embodiments, the dynamic transition model 370 additionally incorporates information about the type of radiation treatment, patient-specific positions, and/or external controls. The dynamic transition model 370 may also include sequences of patient positions that have a low probability of occurring. These sequences, e.g., in a breathing movement, comprise a cough, a hiccup, a sneeze, or the like.

In some embodiments, patient-specific data from which sequences of patient positions can be identified is available. The patient-specific data can be combined with data collected from other patients in the dynamic transition model 370. In these embodiments, the patient-specific data has a higher probability of actually occurring than the non-patient specific data.

In an exemplary embodiment, the dynamic transition model 370 includes information about a radiation treatment in which radiation is delivered when the patient inhales but not when the patient exhales. In this embodiment, a sequence comprising a first inhale position and a second inhale position is given a higher probability than a sequence which comprises an exhale position followed by an inhale position.

In one embodiment, the stochastic patient movement model module 310 stores position data as a two-dimensional matrix. The first dimension (i.e., columns) corresponds to the time slots of the radiation treatment. The second dimension (i.e., rows) corresponds to possible patient positions. The values in the matrix represent a probability that the patient will be in a position, $p_n$, at a time slot, $t_n$. Ideally, the probability values in each column (i.e., time slot) add up to 1, or a 100% probability. As will be apparent to those skilled in the art, other data structures, such as a data tree, may be used.

The accumulated dosage calculator 320 is configured to calculate accumulated dosages based on the identified sequences of patient positions and a dosage delivery model. The accumulated dosage calculator 320 is configured to receive a dosage delivery model comprising treatment information corresponding to time slots within the radiation treatment.

As is known in the art, the dosage delivery model specifies a dosage level and a location corresponding to each time slot. The dosage level typically includes a shape of a beam of radiation, modulation of the beam, and intensity of the beam. The location indicates where the beam of radiation is directed at a point in time and depends, at least in part, on the position of a gantry such as Gantry 210.

The accumulated dosage calculator 320 is configured to sum expected dosages at each time slot based on the dosage delivery model specified location and the patient position within a sequence of patient positions. To illustrate, the accumulated dosage calculator 320 receives a sequence of patient positions each corresponding to a time slot and a dosage delivery model having a dosage level and a location each corresponding to a time slot. At each time slot, using techniques known to those skilled in the art, an expected dosage is calculated indicating how much radiation will be received by a target volume. The expected dosages calculated for each patient position in each of the time slots within a given sequence of patient positions are then summed to calculate the accumulated dosage.

The probability module 330 is configured to correlate the probability of the sequence of patient positions to the accumulated dosage. The correlation is performed based on the assumption that the patient position during the radiation treatment directly affects the amount of radiation actually received by a target volume. As described herein, with respect to the stochastic patient movement model module 310, each sequence of patient positions has a specified probability based on the initial phase probability model and the dynamic transition model. When the accumulated dosage calculator 320 calculates the accumulated dosage based on the sequence of patient positions and a dosage delivery model, the probability module 330 correlates the probability for the sequence of patient positions to the accumulated dosage.

The optional probability dosage volume histogram module (PDVH module) 340 is configured to generate a probability dosage volume histogram based on multiple accumulated dosages and the correlated probabilities for a target volume based on a dosage delivery model. The target volume may include, e.g., a cancerous tumor, an organ, or the spinal cord. In some embodiments, the PDVH module 340 is configured to, based on the correlated probabilities, determine whether the accumulated dosages are within a specified confidence interval, such as a 95% confidence interval. The probability dosage volume histogram is further discussed in connection with FIG. 5.

Figure 4:
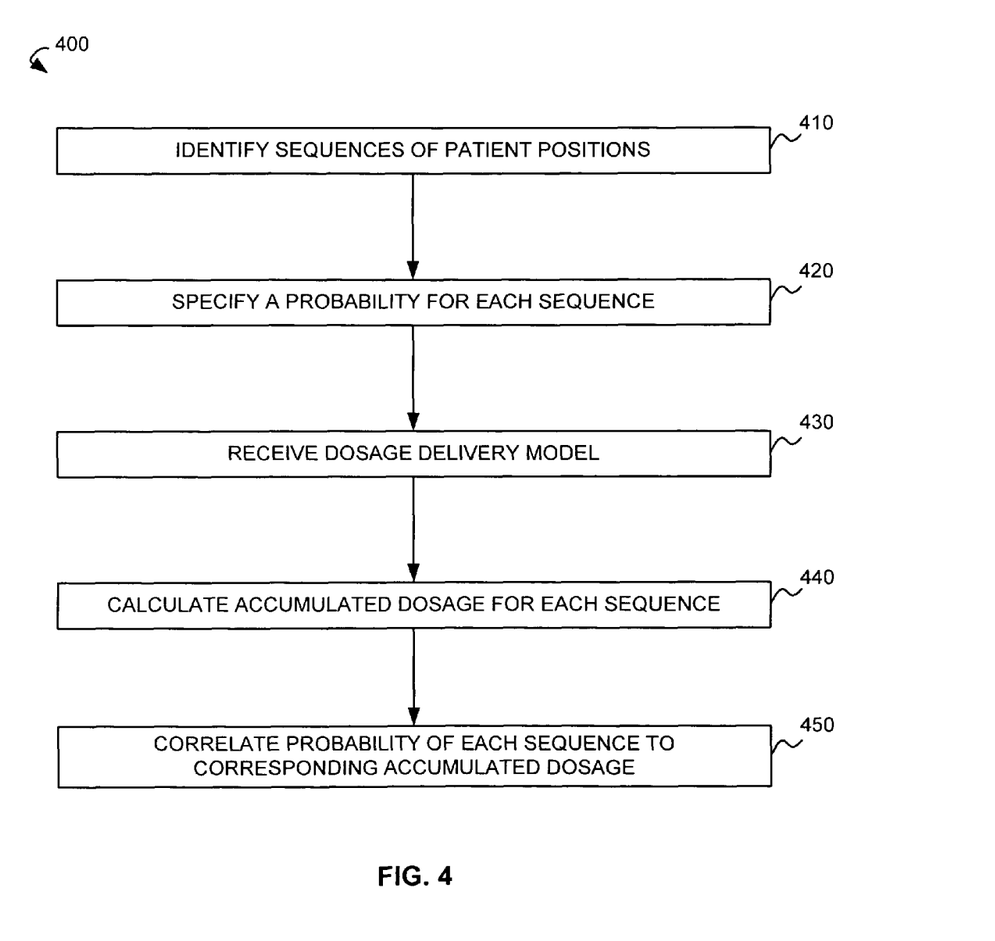
FIG. 4 is a flowchart of an exemplary method of calculating an accumulated dosage correlated to a probability based on patient positions according to various embodiments of the invention.

FIG. 4 is a flowchart of an exemplary method 400 of calculating a accumulated dosage correlated to a probability based on a sequence of patient positions according to various embodiments of the invention. The method 400 may be performed by the probabilistic dosage engine 300.

In a step 410, sequences of patient positions are identified. The sequences are identified based on an ideal movement model, an initial phase probability model, and a dynamic transition model. In the sequences of patient positions, each position corresponds to a time slot.

In a step 420, probabilities are specified for each of the sequences of patient positions. The probability of a sequence of patient positions is a probability of the sequence of patient positions actually occurring during a radiation treatment.

In a step 430, a dosage delivery model is received. The dosage delivery model specifies a dosage level and a location corresponding to each time slot of the radiation treatment. The time slots in the sequences of patient positions correspond to the time slots within the dosage delivery model.

In a step 440, an accumulated dosage is calculated for each sequence of patient positions. In some embodiments, the accumulated dosage is calculated only if the probability for a sequence meets a predetermined threshold. The accumulated dosage is calculated as described in connection with the accumulated dosage calculator 320.

In a step 450, the probability of each sequence is correlated to the accumulated dosage calculated from the sequence. The correlated probability indicates the likelihood that the target volume will receive the accumulated dosage.

Figure 5:
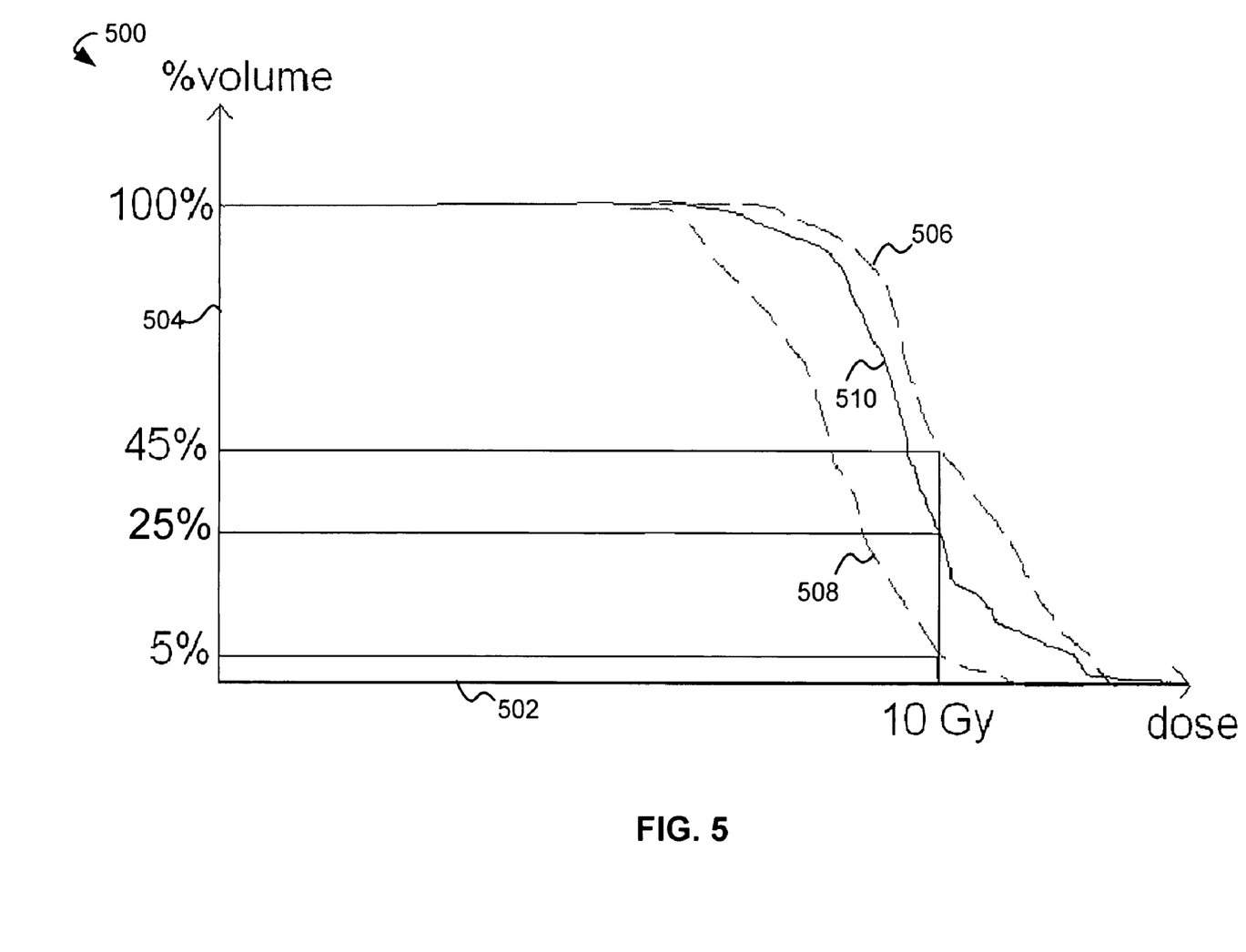
FIG. 5 is a probabilistic dosage volume histogram according to various embodiments of the present invention.

FIG. 5 is an exemplary probabilistic dosage volume histogram 500 as may be generated by the PDVH module 340 according to various embodiments of the present invention. The probabilistic dosage volume histogram 500 has an x-axis 502 corresponding to a dosage level (in Grays) and a y-axis 504 corresponding to a percent volume of the target volume. The probabilistic dosage volume histogram 500 includes accumulated dosages based on a 95% confidence interval. The probability information comprises an upper probable dosage curve 506 and a lower probable dosage curve 508. In the depicted embodiment, a median dosage curve 510 is also included. The probabilistic dosage volume histogram 500 may be interpreted as "at maximum, within a 95% confidence interval, the dosage of at least ten Grays is received by 45% of the total volume of the organ in question; at minimum, within a 95% confidence interval, the dosage of at least 10 Grays is received by 5% of the total volume of the organ in question; and the median dosage of at least ten Grays is received by 25% of the total volume of the organ in question."

In some embodiments, multiple probabilistic dosage volume histograms are generated for a dosage delivery plan. The multiple probabilistic dosage volume histograms each correspond to separate organs and/or target volumes. Further, multiple dosage delivery models may be evaluated by generating probabilistic dosage volume histograms based on each of the dosage delivery models. Thus, a doctor can evaluate the multiple probabilistic dosage volume histograms in order to select a preferred dosage delivery model.

Further, because probability information is included in the probabilistic dosage volume histogram 500, it is possible to deduce a relative sensitivity of a dosage delivery model to patient movement. For example, if there is a large amount of variation between the upper probable dosage curve 506 and the lower probable dosage curve 508, the dosage delivery model is more sensitive to changes in patient positions than a dosage delivery model having a smaller amount of variation between the upper probable dosage curve 506 and the lower probable dosage curve 508. This information may be helpful, for example, to assure that a minimum dose is received with at least a 95% probability.

Several embodiments are specifically illustrated and/or described herein. However, it will be appreciated that modification and variations are covered by the above teachings and within the scope of the appended claims without departing from the spirit and intended scope thereof. Further, various embodiments of the invention include computing instructions configured to perform various methods and functions described herein, and stored on a computer read readable media. For example, the information produced using the methods discussed herein may be used as a starting point for other algorithms, or can be stored for later used.

The embodiments discussed herein are illustrative of the present invention. As these embodiments of the present invention are described with reference to illustrations, various modifications or adaptations of the methods or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

What is claimed is:

1. A method comprising:
identifying a first sequence of patient positions each corresponding to a time slot based on an ideal movement model, an initial phase probability model, and a dynamic transition model;
identifying a second sequence of patient positions each corresponding to a time slot based on the ideal movement model, the initial phase probability model, and the dynamic transition model;
specifying a first probability for the first sequence of patient positions;
specifying a second probability for the second sequence of patient positions;
receiving a first dosage delivery model specifying a dosage level and a location corresponding to each time slot;
calculating a first accumulated dosage for the first sequence of patient positions based on the first dosage delivery model;
calculating a second accumulated dosage for the second sequence of patient positions based on the first dosage delivery model, wherein the act of calculating the second accumulated dosage is performed using a processor;
correlating the first probability of the first sequence of patient positions to the first accumulated dosage; and
correlating the second probability of the second sequence of patient positions to the second accumulated dosage.

2. The method of claim 1, wherein the act of calculating the first accumulated dosage is performed by summing an expected dosage at each time slot based on the first dosage delivery model specified location and the patient position within the first sequence of patient positions.

3. The method of claim 1, wherein the act of calculating the second accumulated dosage is performed by summing an expected dosage at each time slot based on the first dosage delivery model specified location and the patient position within the second sequence of patient positions.

4. The method of claim 1, further comprising creating a probability dosage volume histogram based on the first accumulated dosage, the second accumulated dosage, the correlated first probability, and the correlated second probability.

5. The method of claim 1, further comprising:
receiving a second dosage delivery model specifying another dosage level and another location corresponding to each time slot;
calculating a third accumulated dosage for the first sequence of patient positions based on the second dosage delivery model;
calculating a fourth accumulated dosage for the second sequence of patient positions based on the second dosage delivery model;
correlating the first probability of the first sequence of patient positions to the third accumulated dosage; and
correlating the second probability of the second sequence of patient positions to the fourth accumulated dosage.

6. The method of claim 5, further comprising creating a probability dosage volume histogram based on the third accumulated dosage, the fourth accumulated dosage, the correlated first probability, and the correlated second probability.

7. The method of claim 1, wherein the patient positions comprise a location of a target volume within a patient.

8. The method of claim 1, wherein the first sequence of patient positions and the second sequence of patient positions are identified based on a type of treatment.

9. The method of claim 1, wherein the first probability is based on an external control of the sequence of patient positions.

10. The method of claim 1, wherein the first probability is based on patient-specific data.

11. The method of claim 1, wherein the act of calculating a first accumulated dosage is based on whether the first probability exceeds a threshold.

12. The method of claim 1, wherein the first sequence of patient positions is nearly continuous.

13. The method of claim 1, wherein the first sequence of patient positions comprises a plurality of discrete patient positions.

14. The method of claim 1, wherein the first sequence of patient positions comprises patient positions during a breathing cycle.

15. The method of claim 1, further comprising administering dosages in the dosage delivery model to a patient during intensity modulated radiation therapy.

16. A system comprising:
    a stochastic patient movement model module configured to identify a first sequence of patient positions each corresponding to a time slot and a second sequence of patient positions each corresponding to a time slot based on an ideal movement model, an initial phase probability model, and a dynamic transition model, and specify a first probability for the first sequence of patient positions and a second probability for the second sequence of patient positions;
    an accumulated dosage calculator configured to calculate a first accumulated dosage for the first sequence of patient positions based on a dosage delivery model specifying a dosage level and a location corresponding to each time slot and a second accumulated dosage for the second sequence of patient positions based on the dosage delivery model, wherein the accumulated dosage calculator comprises a processor; and
    a probability module configured to correlate the first probability of the first sequence of patient positions to the first accumulated dosage and correlate the second probability of the second sequence of patient positions to the second accumulated dosage.

17. The system of claim 16, wherein the accumulated dosage module is configured to sum an expected dosage at each time slot based on the dosage delivery model specified location and the patient position within the first sequence of patient positions.

18. The system of claim 17, further comprising a probability dosage volume histogram module configured to create a probability dosage volume histogram based on the first accumulated dosage, the second accumulated dosage, the correlated first probability, and the correlated second probability.

19. A computer-readable product having a non-trasitory medium storing instructions executable by a processor for performing a method for calculating accumulated dosages based on patient movement, the method comprising:
    identifying a first sequence of patient positions each corresponding to a time slot based on an ideal movement model, an initial phase probability model, and a dynamic transition model;
    identifying a second sequence of patient positions each corresponding to a time slot based on the ideal movement model, the initial phase probability model, and the dynamic transition model;
    specifying a first probability for the first sequence of patient positions;
    specifying a second probability for the second sequence of patient positions;
    receiving a dosage delivery model specifying a dosage level and a location corresponding to each time slot;
    calculating a first accumulated dosage for the first sequence of patient positions based on the dosage delivery model;
    calculating a second accumulated dosage for the second sequence of patient positions based on the dosage delivery model;
    correlating the first probability of the first sequence of patient positions to the first accumulated dosage; and
    correlating the second probability of the second sequence of patient positions to the second accumulated dosage.

20. The computer readable medium of claim 19, wherein the act of calculating the first accumulated dosage is performed by summing an expected dosage at each time slot based on the dosage delivery model specified location and the patient position within the first sequence of patient positions.

* * * * *